United States Patent [19]

Ellison

[11] Plant 4,999

[45] Mar. 15, 1983

[54] ASPARAGUS PLANT NO. 22

[75] Inventor: J. Howard Ellison, Milltown, N.J.

[73] Assignee: Research Corporation, New York, N.Y.

[21] Appl. No.: 226,858

[22] Filed: Jan. 21, 1981

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

An asparagus plant having particularly valuable male characteristics and suitable for use in production of edible spears and of hybrids since it transmits high yield, rust resistance, and good field tolerance to root rot (*Fusarium oxysporum*) and crown rot (*F. moniliforme*) which would otherwise limit production, enabling growth where standard susceptible cultivars cannot be grown profitably.

2 Drawing Figures

BACKGROUND OF THE INVENTION

The asparagus industry has over the years suffered from a number of problems, not the least of which is the common disregard for disease prevention, and resultant wide epiphytotics with Fusarium fungus, which has reduced production to a point where drastic improvement is desirable, and is the target of most aspects of the instant invention.

A continuing program of intensive breeding and selection has been carried on by me over a long period of time in which I have devoted virtually all my skill and knowledge to the improvement of the basic plants and necessarily and particularly to the male and female plants as individuals, as well as the seeds, since the ultimate production of asparagus currently depends on plants produced from the seeds collected, planted and carefully grown into plants which will produce asparagus in the quantities and of the quality acceptable to and demanded by the ultimate consumer.

Interestingly enough the concept above suggested, which while not unknown, has caused me to devote a great deal of time to the breeding and selection of male and female varieties which will provide the attributes sought, in this particular instance a male asparagus variety being the subject of the further description and disclosure herein.

This new and distinct male asparagus variety is denominated as No. 22 for the purposes hereof, and for reference to my records in relation thereto.

The particular plant which I first discovered and which serves as a basis for the invention hereof, was selected a number of years ago for its rust resistance and its obvious distinction from surrounding plants, and as a matter of fact because it did have 58 stalks, three of which were 19,17 and 16 mm in diameter 2.5 cm above the ground.

One of the factors which made this particular plant outstanding was that it was growing in a very old field and it was apparently resisting rust very well to grow in this manner.

Subsequently I asexually reproduced the plant by tissue culture, specifically meristem culture, and I have found that the aforementioned characteristics have come true in successive propagations.

One of the valuable characteristics of the particular plant under consideration and thus as a variety developed hereby, is that it is vigorous, as apparent from the plant discovered, and it has continued to maintain this characteristic, making it useful for growing edible spears.

Certain other qualities which may be attributed to this variety include high yield, rust resistance to (*Puccinia asparagi*) and good field tolerance to root rot (*Fusarium oxysporum*) as well as crown rot (*F. moniliforme*).

I note in the course of my experimenting with asparagus plants over many years, and the subsequent discovery of this particular variety, that the same was selected from a large group of the variety Mary Washington (unpatented) which was at one time a relatively clean strain. However, the practice of seed collection without careful selection, and planting by growers from mature Mary Washington plants eventually resulted in deterioration of the genetic quality and thus production.

The plants in the area from which the plant hereof was selected were growing in a large old cultivated field near Sharptown, N.J. The particular plants in the area were inspected, and the one herein described carefully chosen and in turn reproduced by asexual reproduction for the qualities previously set forth, having regard for the fact that there are many distinctions among various asparagus varieties including color, although color is not the most outstanding such distinction. There are also specific characteristics determined by dimensions, position of nodes, branches, height, diameter of stalk as well as production yield which have been accumulated as a measure of the value of this particular variety.

In this instance the variety hereof is used as the pollen parent to produce seed to replenish or establish new asparagus fields, the importance of rust resistance and tolerance to root and crown rot being of substantial consideration. Where these attributes or even certain of them have been found in a variety, it is useful to avail of the same for seed production.

Specifically the following table of averages, developed from a study of a large number of asparagus plants of this No. 22 variety, assists me in identifying the same and assures me of the continuing maintenance of the best attributes as well as substantially conforming to the originally discovered and subsequently manipulated plants selected for what I have found are desirable characteristics.

| | |
|---|---|
| Number of nodes below first branch | 20.9 |
| Number of cm from Crown to first branch | 55.1 |
| Number of Branches | 57.3 |
| Number of cm between first and last branch | 140.2 |
| Number of Cladophyll nodes beyond last branch | 37.7 |
| Number of cm beyond last branch | 24.3 |
| Diameter (mm) highest head stalk | 16.0 |
| Diameter (mm) largest stalk | 18.4 |
| Internode length (cm) between branches | 2.44 |
| Internode length (cm) beyond last branch | .64 |

Appended hereto is a drawing which shows a typical plant of this variety No. 22, as it grows during the summer, and used as a basis for the foregoing table.

The general color of the variety is difficult to determine as being a single color since it varies over a rather wide range from the densest part of the plant to the extremities of the various branches. Thus no single color of the plant is noted for comparison with a color scale of any known accepted source. However, when a single stalk is compared using the Munsell Color Cascade published by Macbeth Division of Kollmorgen Corporation, with the bloom removed, the notation 22-12 in said Cascade appears most nearly appropriate.

While it is virtually impossible to conclude that the particular color is precisely depicted in an illustration of the kind herein due to the nature of asparagus generally, it does appear that the plant hereof, includes stalks most nearly conforming to the above suggested color notation.

It may be specifically pointed out that this color comparison is made from a two inch segment of the stalk below the lowest branch, with the waxy covering or bloom which would otherwise obscure such color, having been removed.

The really outstanding differences in the subject variety from others may be found in the table of averages supplied, and it is appropriate to point out that certain of the aspects, such as the distance between the first and last branch, the first branch being the bottom branch or lowest branch, in a typical plant of my new variety, is actually greater, on the order of nearly 30%, than a typical Mary Washington plant at about the same time of its growth during the year.

It is also noted that the variety hereof has nearly double the number of cladophyll nodes on the main stalk beyond the last branch, on which such nodes appear, as compared with Mary Washington.

The distance beyond the last branch on which the cladophyll nodes appear in my new variety, is more than double that of Mary Washington.

Comparing the stalk color of my new variety, with the bloom removed, as similarly treated, indicates a slight difference with Mary Washington, the Mary Washington stalk color of similar proportion, using the Munsell Color Cascade being about 23-12.5.

The flowers of the plant may be described as including yellow petal tips notation 24-4, with the green rib of the petal 22-9. The yellow petal tip refers to the blossom ends of the petals, approximately half way to the base. The green rib of the petal refers to the mid rib of the petal which extends from the base to approximately three-fourths the length of the petals. The extreme basal portion of the petals also is the same shade of green.

It can be seen that the instant variety, does in fact have substantial differences from a known variety, those noted being the most outstanding, and in fact differs from other varieties of my own development in similar respects.

There are some similarities, such as the fact that the number of branches is about the same in my new variety as compared with the Mary Washington variety. It is also notable that the diameter of the highest headed stalk in my new variety is about the same as the Mary Washington variety.

The various dimensional notations in the table previously set forth, are considered in the light of the drawing comprising a part hereof which discloses a typical asparagus plant in which the titles of the notations are disclosed.

I have found that identification of asparagus plants which I have developed, may be materially assisted by using this table and in fact affords a basis for distinguishing my new variety from other similar, even related varieties.

I claim:

1. A new and distinct variety of male asparagus plant, substantially as herein shown and described, characterized particularly as to novelty by the unique combination of rust resistance (*Puccinia asparagi*), good field tolerance to root rot (*Fusarium oxysporum*) and crown rot (*F. moniliforme*), its ability to produce edible spears and to be combined with a female plant to produce hybrid seed which will produce plants having useful production characteristics.

* * * * *

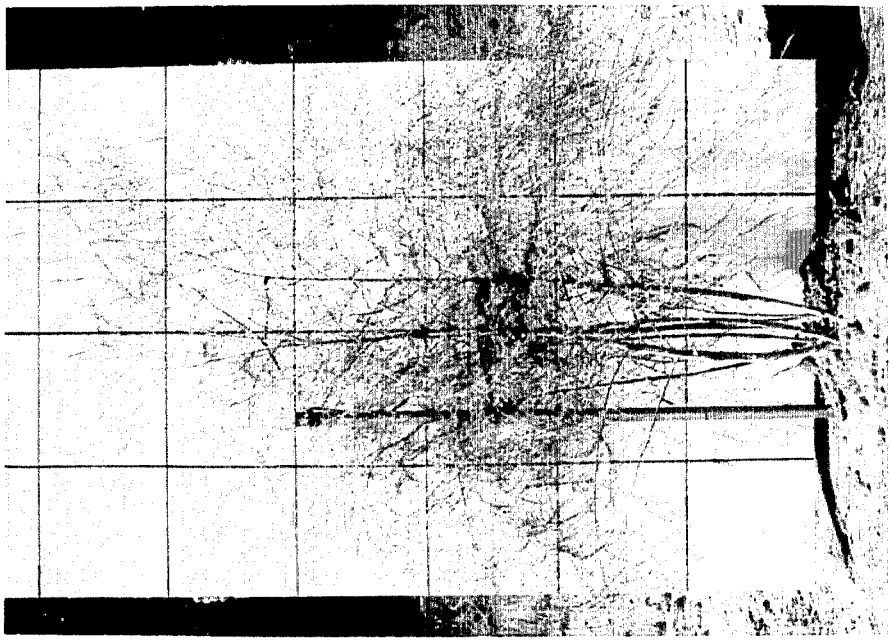
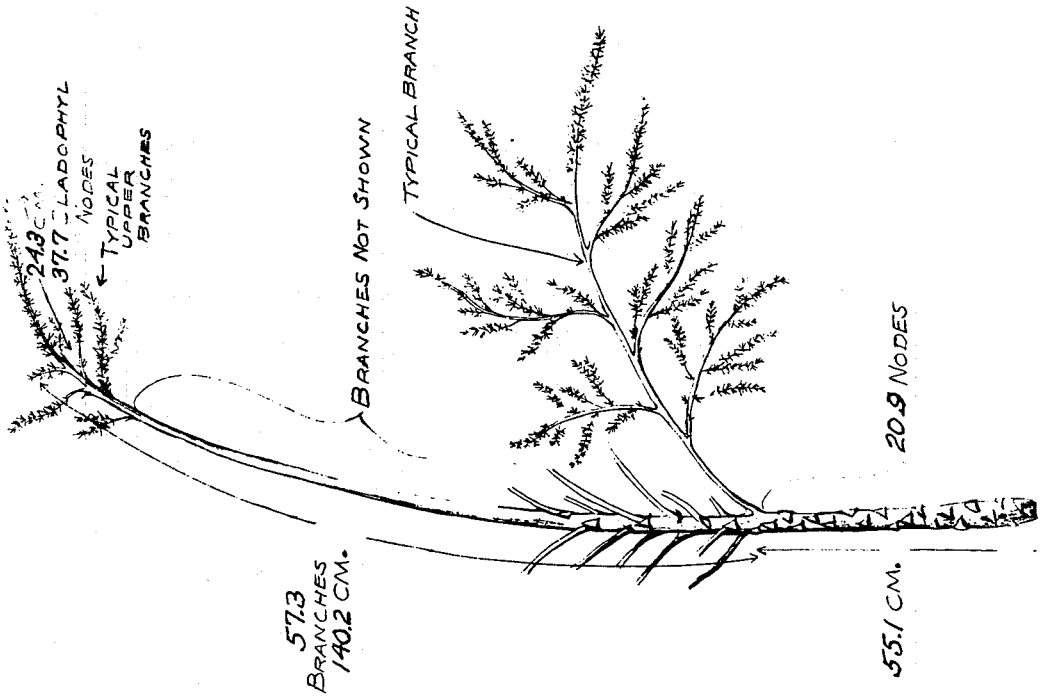
24.3 CM.
37.7 CLADOPHYL NODES
TYPICAL UPPER BRANCHES
BRANCHES NOT SHOWN
TYPICAL BRANCH
57.3 BRANCHES 140.2 CM.
20.9 NODES
55.1 CM.